US012751763B2

(12) United States Patent
Daniel et al.

(10) Patent No.: US 12,751,763 B2
(45) Date of Patent: Oct. 6, 2026

(54) CATHETER WITH FLEX CIRCUIT DISTAL ASSEMBLY

(71) Applicant: BIOSENSE WEBSTER (ISRAEL) LTD., Yokneam (IL)

(72) Inventors: Steven A. Daniel, Azusa, CA (US); Daniele Ghidoli, Laguna Hills, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 392 days.

(21) Appl. No.: 18/197,559

(22) Filed: May 15, 2023

(65) Prior Publication Data

US 2023/0277239 A1 Sep. 7, 2023

Related U.S. Application Data

(63) Continuation of application No. 16/228,609, filed on Dec. 20, 2018, now Pat. No. 11,648,053.

(51) Int. Cl.

*A61B 18/00* (2006.01)
*A61B 18/14* (2006.01)
*A61B 90/00* (2016.01)

(52) U.S. Cl.

CPC ..................... *A61B 18/1492* (2013.01); *A61B 2018/00029* (2013.01); *A61B 2018/00357* (2013.01); *A61B 2018/00577* (2013.01); *A61B 2018/00821* (2013.01); *A61B 2218/002* (2013.01)

(58) Field of Classification Search

None

See application file for complete search history.

(56) References Cited

U.S. PATENT DOCUMENTS

| | | | | |
|---|---|---|---|---|
| 5,334,193 | A | 8/1994 | Nardella | |
| 5,423,807 | A | 6/1995 | Milder | |
| 5,685,878 | A | 11/1997 | Falwell et al. | |
| 5,687,723 | A * | 11/1997 | Avitall | A61B 18/1492 606/41 |
| 5,954,719 | A | 9/1999 | Chen et al. | |
| 6,017,338 | A | 1/2000 | Brucker et al. | |
| 6,156,034 | A | 12/2000 | Cosio et al. | |
| 6,350,262 | B1 | 2/2002 | Ashley | |
| 6,506,189 | B1 | 1/2003 | Rittman, III et al. | |
| 7,584,005 | B1 | 9/2009 | Jain | |

(Continued)

OTHER PUBLICATIONS

Annotated Kassab Fig 6 (Year: 2025).*

(Continued)

*Primary Examiner* — Joanne M Rodden
*Assistant Examiner* — Nicholas S Borsch
(74) *Attorney, Agent, or Firm* — FBT Gibbons LLP

(57) ABSTRACT

An electrophysiology catheter has an elongated catheter shaft and a distal assembly with a flex circuit and a support member on which the flex circuit is supported in a generally cylindrical form. The support member has a post extending longitudinally through the cylindrical form of the flex circuit which delivers irrigation fluid into the cylindrical form. The post can be configured to define multiple irrigation chambers within the distal assembly. One or more flow directors movable in the post selectively direct irrigation fluid within the distal assembly. Apertures in the flex circuit allow the irrigation fluid to exit to outside the distal assembly.

19 Claims, 15 Drawing Sheets

(56) References Cited

U.S. PATENT DOCUMENTS

| | | | | |
|---|---|---|---|---|
| 7,857,810 | B2 * | 12/2010 | Wang | A61B 18/148 606/41 |
| 7,917,229 | B2 | 3/2011 | Zarembo et al. | |
| 7,959,628 | B2 | 6/2011 | Schaer et al. | |
| 8,221,409 | B2 | 7/2012 | Cao et al. | |
| 8,323,279 | B2 | 12/2012 | Dahla et al. | |
| 8,357,152 | B2 | 1/2013 | Govari et al. | |
| 8,425,421 | B2 | 4/2013 | Hadjicostis | |
| 8,456,182 | B2 | 6/2013 | Bar-Tal et al. | |
| 8,827,910 | B2 | 9/2014 | de la Rama et al. | |
| 8,882,755 | B2 | 11/2014 | Leung et al. | |
| 8,923,989 | B2 | 12/2014 | Zarembo et al. | |
| 8,979,840 | B2 | 3/2015 | Christian | |
| 9,050,069 | B2 | 6/2015 | Lalonde et al. | |
| 9,186,211 | B2 | 11/2015 | Mathur | |
| 9,622,814 | B2 | 4/2017 | Wang et al. | |
| 2008/0188912 | A1 | 8/2008 | Stone et al. | |
| 2009/0143779 | A1 | 6/2009 | Wang et al. | |
| 2009/0163911 | A1 | 6/2009 | Cao et al. | |
| 2009/0163912 | A1 | 6/2009 | Wang et al. | |
| 2011/0130648 | A1 | 6/2011 | Beeckler et al. | |
| 2012/0071870 | A1 | 3/2012 | Salahieh et al. | |
| 2013/0030426 | A1 | 1/2013 | Gallardo et al. | |
| 2013/0172873 | A1 | 7/2013 | Govari et al. | |
| 2013/0197499 | A1 | 8/2013 | Lalonde et al. | |
| 2014/0081112 | A1 * | 3/2014 | Kim | A61B 5/367 600/374 |
| 2014/0163546 | A1 | 6/2014 | Govari et al. | |
| 2014/0200428 | A1 * | 7/2014 | Kassab | A61B 5/0538 600/547 |
| 2014/0276052 | A1 | 9/2014 | Rankin et al. | |
| 2014/0276759 | A1 | 9/2014 | Kim et al. | |
| 2015/0272665 | A1 | 10/2015 | Govari | |
| 2015/0273184 | A1 | 10/2015 | Scott et al. | |
| 2016/0051321 | A1 | 2/2016 | Salahieh et al. | |
| 2016/0113712 | A1 | 4/2016 | Cheung et al. | |
| 2016/0128765 | A1 | 5/2016 | Schultz et al. | |
| 2016/0228061 | A1 | 8/2016 | Källbäck et al. | |
| 2017/0143414 | A1 | 5/2017 | Sliwa et al. | |
| 2017/0311893 | A1 * | 11/2017 | Beeckler | A61B 5/6857 |
| 2017/0333125 | A1 | 11/2017 | Lepak et al. | |
| 2018/0071017 | A1 | 3/2018 | Bar-Tal et al. | |
| 2018/0110562 | A1 | 4/2018 | Govari et al. | |
| 2020/0197082 | A1 | 6/2020 | Daniel et al. | |

OTHER PUBLICATIONS

European Search Report for EP Application No. 19217909.1 dated Jun. 3, 2020, 7 pages.

U.S. Appl. No. 15/925,521, filed Mar. 19, 2018 entitled Catheter With Multifunctional Microinjection-Molded Housing, 25 pages.

Chinese First Office Action and Search Report dated Nov. 6, 2023, for Application No. 201911323830.7, 8 pages.

Chinese Second Office Action dated May 23, 2024, for Application No. 201911323830.7, 7 pages.

Chinese Third Office Action and Search Report dated Jul. 16, 2024, for Application No. 201911323830.7, 8 pages.

European Communication dated Feb. 22, 2023, for Application No. 19217909.1, 5 pages.

Japanese First Office Action dated Sep. 12, 2023, for Application No. 2019-229104, 3 pages.

* cited by examiner

CATHETER WITH FLEX CIRCUIT DISTAL ASSEMBLY

CROSS-REFERENCE TO RELATED APPLICATION(S)

The present application is a continuation of U.S. patent application Ser. No. 16/228,609, filed Dec. 20, 2018, now U.S. Pat. No. 11,648,053, the content of which is incorporated herein by reference.

FIELD OF INVENTION

The present description relates generally to electrophysiology catheters, and in particular, irrigated ablation catheters.

BACKGROUND OF INVENTION

Medical procedures involving ablation of the heart may be used to cure a variety of cardiac arrhythmia, as well as to manage atrial fibrillation. Such procedures are known in the art. Other medical procedures using ablation of body tissue, such as treating varicose veins, are also known in the art. The ablation energy for these procedures may be in the form of radio-frequency (RF) energy, which is supplied to the tissue via one or more electrodes of a catheter used for the procedures.

The application of the ablation energy to body tissue, if uncontrolled, may lead to an unwanted increase of temperature of the tissue resulting in charring, thrombosis and other complications, especially where a portion of the ablating electrode is buried in tissue. It is consequently important to control the temperature of the tissue during any medical procedure involving ablation. One method for control is to irrigate the tissue being ablated. However, irrigation requires components to deliver fluid from a proximal end of the catheter to its distal end. With catheter distal ends having diameters on the order of millimeters, space is often a primary constraint on the design and configuration of distal ends that provide for fluid delivery components. Moreover, with distal ends having tip and ring electrodes, such fluid delivery components must define fluid pathways that can provide axial flow and radial flow but occupy minimal space and avoid interfering with other functional aspects of the distal end, such as force sensing and temperature sensing. As such, assembling a catheter distal tip on a micro-level with multiple parts and components can be labor intensive and costly.

Flex circuits or flexible electronics involve a technology for assembling electronic circuits by mounting electronic devices on flexible plastic substrates, such as polyimide, Liquid Crystal Polymer (LCP), PEEK or transparent conductive polyester film (PET). Circuits or traces can be screen printed onto the substrates, or applied by photolithographic or 3-D printing technology, to offer an assortment of microelectronic features that are carried on the flex circuit.

Applicants recognized that there is a need to provide a catheter with a distal assembly that can be used to ablate with irrigation for temperature control yet be more easily manufactured and assembled, especially incorporating a flex circuit that provides multiple microelectronic features, for example, electrodes and thermocouples for contact with tissue in diagnostic and therapeutic procedures.

SUMMARY OF THE DISCLOSURE

An electrophysiology catheter has a distal assembly that can ablate with fluid irrigation and temperature sensing while embodying a configuration that supports the use of a flex circuit which enables manufacturing and assembly in a high-volume, low cost manner. An irrigated ablation distal assembly of this configuration can be readily assembled to present a structurally sound construction. The flex circuit with its traces can provide ablation surfaces or temperature sensing surfaces in multiple configurations, as desired or appropriate. Moreover, the flex circuit is supported and carried on a support structure or "bobbin" that allows circulation of irrigation fluid throughout the distal assembly to aid in maintaining a desired thermal energy level within the distal assembly and the supported structure can be made of less-costly material, including plastic, which can be readily constructed with micro-injection molding. Both the flex circuit and the support structure incorporate features that enable irrigation fluid to enter and exit the distal assembly in cooling the distal assembly and surrounding tissue and bodily fluids. One or more flow directors are adjustable in the support member to direct irrigation fluid selectively to different irrigation chambers or in different directions within the distal assembly. Accordingly, the distal assembly leverages the flex circuit and assembly configuration with the ability to provide improved thermal control and cooling with thermally conductive elements and adjustable irrigation fluid delivery providing effective heat transfer and thermal management to facilitate effective ablation while minimizing fluid load on the patient.

In some embodiments, the electrophysiology catheter includes an elongated catheter shaft, and a distal assembly defining a longitudinal axis. The distal assembly includes a flex circuit and a support member. The flex circuit is configured in a generally cylindrical form on the support member, with its distal and proximal edge portions supported and affixed to the support member in providing the distal assembly with a circumferential contact surface and internal irrigation chambers. The support member includes a post that extends longitudinally through the cylindrical form of the flex circuit which supports the flex circuit and allows irrigation fluid to enter and circulate within the distal assembly.

In some embodiments, the flex circuit includes an outer surface with electrical traces configured for contact with tissue.

In some embodiments, the flex circuit includes a distal portion and a proximal portion, the distal portion including a generally circular portion and the proximal portion including a generally rectangular portion. The generally circular portion may include radiating arm portions.

In some embodiments, the traces include a thermocouple.

In some embodiments, the traces include an electrode.

In some embodiments, the flex circuit includes a substrate with one or more irrigation apertures.

In some embodiments, the flex circuit includes irrigation openings that are fully or partially covered with a conductive, thermally or otherwise, coating, plating, or the like.

In some embodiments, the post includes a sidewall defining a fluid channel and the sidewall has one or more irrigation apertures in communication with the fluid channel.

In some embodiments, the post includes a raised portion extending in one or more radial direction.

In some embodiments, the post includes one or more raised portion contacting an inner surface of the flex circuit.

In some embodiments, the post includes a raised band extending circumferentially around the post.

In some embodiments, the raised band includes one or more irrigation apertures.

In some embodiments, the distal assembly includes one or more irrigation chambers between the flex circuit and the post.

In some embodiments, a gap space between the flex circuit and the post provides one or more irrigation chambers.

In some embodiments, the post includes a raised band extending circumferentially around the post such that the raised band divides the irrigation chamber into a distal chamber and a proximal chamber.

In some embodiments, the support member includes a flow director in the fluid channel of the post and is configured to move longitudinally in the fluid channel relative to the support member.

In some embodiments, the flow director includes a tubing with a lumen.

In some embodiments, the tubing of the flow director extends from the catheter shaft into the distal assembly.

In some embodiments, the distal assembly includes a cap distal of the support member.

In some embodiments, the distal assembly includes a tip electrode distal of the support member.

In some embodiments, the tip electrode has a dome configuration.

In some embodiments, the tip electrode has an irrigation aperture.

In some embodiments, an electrophysiology catheter has an elongated catheter shaft and a distal assembly defining a longitudinal axis and having a flex circuit and a support member. The flex circuit is configured in a generally cylindrical form on the support member, and has distal and proximal edge portions and a first plurality of irrigation apertures. The support member has a distal member with a distal circumferential surface, and a proximal member with a proximal circumferential surface, and also a post extending between the distal member and the proximal member. The post extends longitudinally through the cylindrical form, with the distal circumferential surface supporting the distal edge portion of the flex circuit and the proximal circumferential surface supporting the proximal edge portion of the flex circuit. The post also has a longitudinal channel surrounded by a sidewall configured with a second plurality of irrigation apertures. The inner surface of the flex circuit and the sidewall of the post define one or more irrigation chambers in fluid communication with the first and second irrigation apertures.

In some embodiments, the distal assembly includes a first flow director in the longitudinal channel. The flow director is configured to move longitudinally within the channel relative to the support member.

In some embodiments, the flow director includes a tubing with a lumen.

In some embodiments, the distal assembly includes a second flow director nested in the longitudinal channel of the first flow director and is rotationally movable about its axis relative to the first flow director.

In some embodiments, the first flow director has irrigation apertures in multiple radial directions and the second flow director has an irrigation formation that can be aligned with selected irrigation apertures of the first flow director depending on the rotational position of the second flow director.

In some embodiments, the sidewall of the post has one or more raised portion configured to contact the flex circuit.

In some embodiments, a raised portion of the post divides an irrigation chamber into at least two irrigation chambers.

In some embodiments, a raised portion extends circumferentially around the post.

In some embodiments, the distal assembly includes a tip electrode mounted on a distal end of the support member.

In some embodiments, the flex circuit includes a distal portion and a proximal portion, the distal portion including a generally circular portion with radiating arm portions, and the proximal portion including a generally rectangular portion.

In some embodiments, an electrophysiology catheter has an elongated catheter shaft and a distal assembly defining a longitudinal axis and having a flex circuit and a support member. The flex circuit is configured in a generally cylindrical form on the support member, and has distal and proximal edge portions and a first plurality of irrigation apertures. The support member has a distal member with a distal circumferential surface, and a proximal member with a proximal circumferential surface, and means for irrigating the distal assembly.

In some embodiments, a method for controlling cooling of a distal assembly of an electrophysiology catheter, comprises adjusting longitudinal movement of a tubular flow director within the distal assembly along a longitudinal axis of the distal assembly. The distal assembly includes a flex circuit and a support member and the flex circuit is configured in a generally cylindrical form along the longitudinal axis on the support member.

In some embodiments, a method of constructing a distal ablation portion of an electrophysiology catheter, includes providing a flex circuit having an inner surface, and an outer surface with electrical traces, and providing a support member having a distal member with a distal circumferential surface, a proximal member with a proximal circumferential surface, and a longitudinal post extending between the distal member and the proximal member. The method also includes wrapping a flex circuit onto the support member with a distal edge portion of the flex circuit affixed to the distal circumferential surface of the support member and a proximal edge portion of the flex circuit affixed to the proximal circumferential surface of the support member.

In some embodiments, the method includes mounting a tip electrode onto a distal end of the support member.

In some embodiments, the tip electrode has a first coupler and the distal end of the support member has a second coupler, and the first and second coupler are configured to couple with each other.

In some embodiments, the post has a fluid channel.

In some embodiments, the method includes inserting a flow director into the fluid channel of the post, the flow director having longitudinal movement in the fluid channel relative to the support member.

In some embodiments, the post of the support member has one or more raised portions configured to contact the inner surface of the flex circuit.

In some embodiments, at least a portion of the inner surface of the flex circuit and the post is separated by a gap space defining an irrigation chamber.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

Overview

Figure 1A:
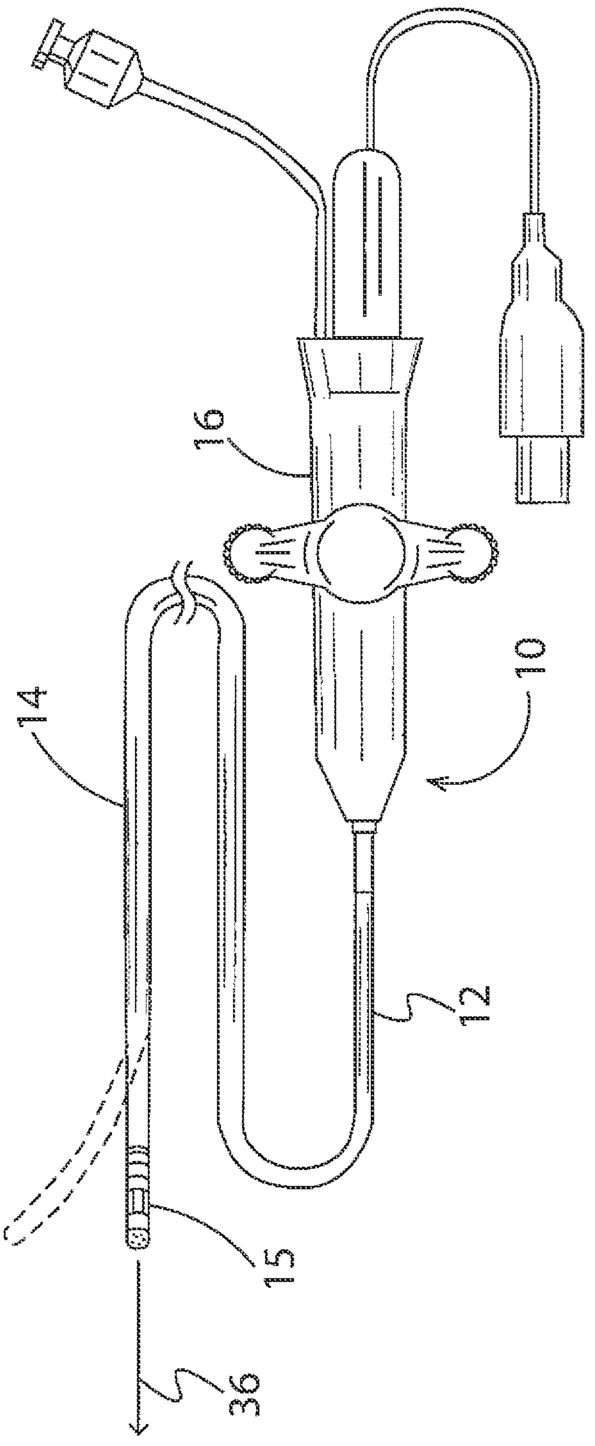
FIG. 1A is a top plan view of a catheter, according to an embodiment.
Figure 1B:
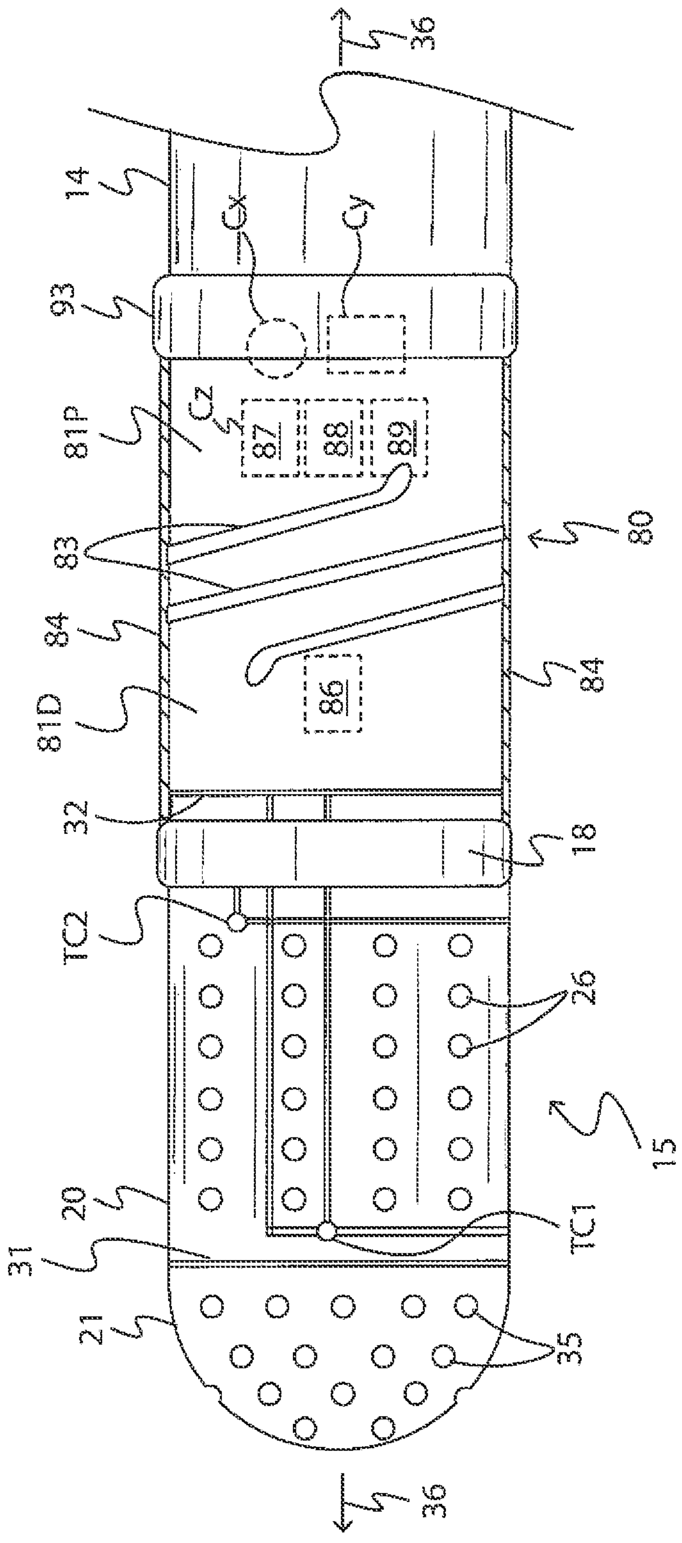
FIG. 1B is a side view of a distal assembly of the catheter of FIG. 1A

With reference to FIG. 1A and FIG. 1B, a catheter 10, which can be used in a minimally invasive procedure such as ablation of cardiac tissue, comprises an elongated catheter shaft 12 and a shorter deflection section 14 distal of the catheter shaft 12, which can be deflected uni-directionally or bi-directionally. Suitable embodiments of the catheter shaft 12 and deflection section 14 are described in U.S. application Ser. No. 15/925,521, filed Mar. 19, 2018, and titled CATHETER WITH MULTIFUNCTIONAL MICROINJECTION-MOLDED HOUSING, the entire disclosure of which is incorporated herein by reference. Distal of the deflection section 14 is a distal assembly 15 which includes at least one electrode and at least one thermocouple. The catheter also includes a control handle 16 proximal of the catheter shaft 12.

The distal assembly 15 advantageously includes a flex circuit 20 and an internal support member 22 (see, e.g., FIG. 3) on to which the flex circuit is applied to provide the distal assembly with a circumferential tissue contact surface and one or more internal chambers for circulating irrigation fluid to cool the flex circuit and the distal assembly. The flex circuit 20 is formed with irrigation apertures 26 so irrigation fluid can exit the distal assembly 15 and also cool surrounding tissue. The distal assembly 15, including the flex circuit 20 and support member 22, facilitates assembly in a manner that can be accomplished with relative ease in an assembly-line fashion, either manually or by automated robotics.

System Description

Figure 2:
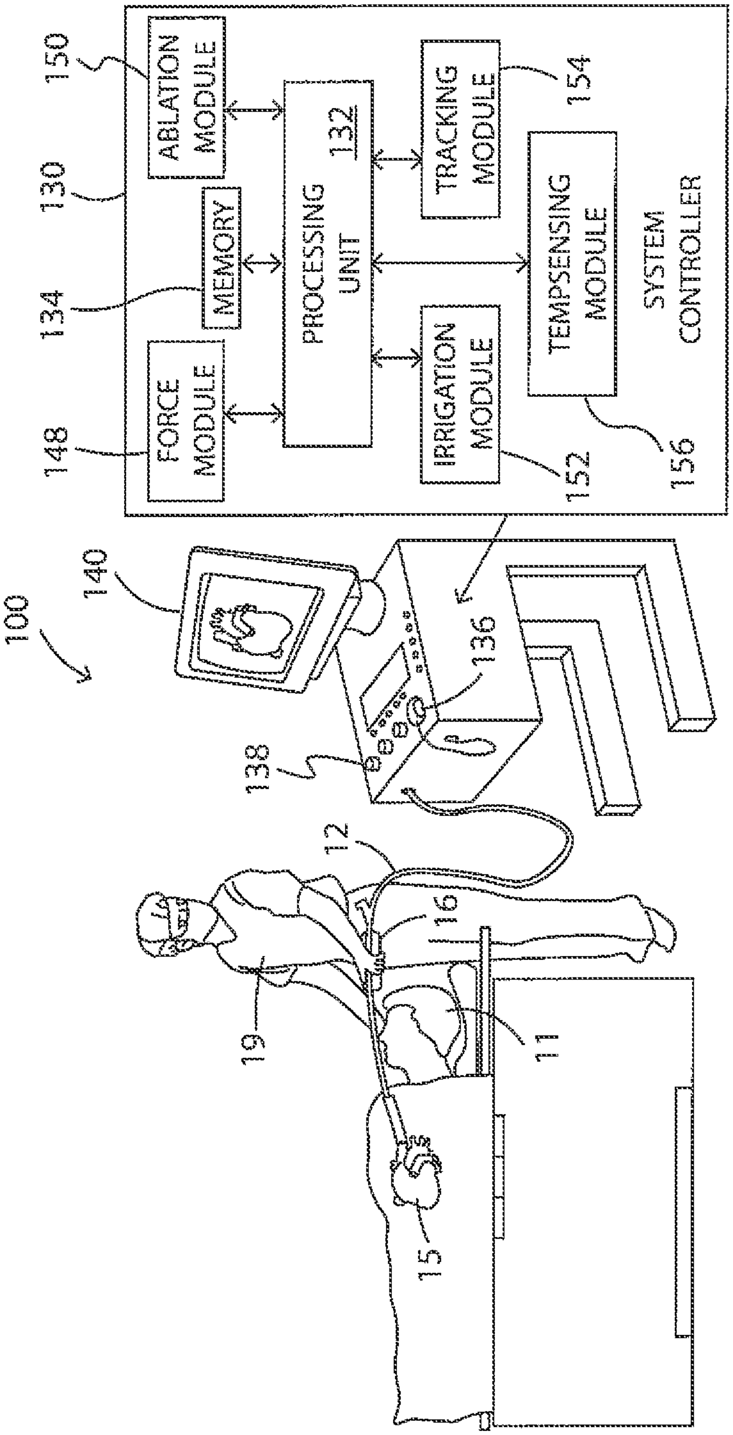
FIG. 2 is a schematic, pictorial illustration of a catheter ablating system, according to an embodiment.

Reference is now also made to FIG. 2, which is a schematic, pictorial illustration of a catheter ablation system 100. In system 100, the catheter 10 is inserted into the vascular system of patient 11 and into a chamber of a heart 13. The catheter is used by an operator 19 of system 100, during a procedure which typically includes performing ablation of the patient's heart tissue. In some embodiments, including use in intracardiac procedures, the catheter shaft 12, the deflection section 14 and distal assembly 15 have a very small outer diameter, typically of the order of 2-3 mm, and all of the internal components of catheter 10, are also made as small and thin as possible and are arranged so as to, as much as possible, avoid damage due to small mechanical strains.

The operations, functions and acts of system 100 are managed by a system controller 130, comprising a processing unit 132 communicating with a memory 134, wherein is stored software for operation of system 100. In some embodiments, the controller 130 is an industry-standard personal computer comprising a general-purpose computer processing unit. However, in some embodiments, at least some of the operations, functions or acts of the controller are performed using custom-designed hardware and software, such as an application specific integrated circuit (ASIC) or a field programmable gate array (FPGA). In some embodiments, the controller 130 is managed by the operator 19 using a pointing device 136 and a graphic user interface (GUI) 138, which enable the operator to set parameters of system 100. The GUI 138 typically also displays results of the procedure to the operator on a display monitor 140.

The software in memory 134 may be downloaded to the controller in electronic form, over a network, for example. Alternatively or additionally, the software may be provided on non-transitory tangible media, such as optical, magnetic, or electronic storage media.

Electrical components, including electrodes, thermocouples and position (location or orientation) sensors, of the distal assembly 15 are connected to system controller 130 by conductors that pass through the catheter shaft 12 and the deflection section 14. In addition to being used for ablation, the electrodes may perform other functions, as is known in the art. The system controller 130 may differentiate between the currents for the different functions of the electrical components by frequency multiplexing. For example, radio-frequency (RF) ablation power may be provided at frequencies of the order of hundreds of kHz, while position sensing frequencies may be at frequencies of the order of 1 kHz. A method of evaluating the position of distal assembly 15 using impedances measured with respect to the electrodes is disclosed in U.S. Pat. No. 8,456,182 titled "Current Localization Tracker," to Bar-Tal et al., the entire disclosure which is incorporated herein by reference.

As shown in FIG. 2, the system controller 130 includes a force module 148, an RF ablation module 150, an irrigation module 152, a tracking module 154 and a temperature sensing module 156. The system control 130 uses the force module 148 to generate and measure signals supplied to, and received from, a force sensor 80 in the distal assembly 15 in order to measure the magnitude and direction of the force on distal assembly 15. The system controller 130 uses the ablation module 150 to monitor and control ablation parameters such as the level of ablation power applied via the one or more electrodes of the distal assembly 15. The ablation module 150 includes an RF generator (not shown) and controls the power/wattage and duration of ablation being applied.

Typically, during ablation, heat is generated in the one or more electrodes energized by the ablation module 150, as well as in the surrounding region. In order to dissipate the heat and to improve the efficiency of the ablation process, the system controller 130 monitors temperature of different portions/surfaces of the distal assembly 15 and supplies irrigation fluid to distal assembly 15. The system controller 130 uses the irrigation module 152 to monitor and control irrigation parameters, such as the rate of flow and the temperature of the irrigation fluid. In some embodiments, the system controller 130 uses the irrigation module 152 in response to the temperature sensing module 156 in managing "hot spots" or uneven heating on the surface of the distal assembly 15, by controlling and adjusting movable internal components of the distal assembly 15, as described in detail further below.

The system controller 130 uses the tracking module 154 to monitor the location and orientation of the distal assembly 15 relative to the patient 11. The monitoring may be implemented by any tracking method known in the art, such as one provided in the Carto3® system manufactured by Biosense Webster of Irvine, CA. Such a system uses radio-frequency (RF) magnetic transmitter external to patient 11 and responsive elements within distal assembly 15. Alternatively or additionally, the tracking may be implemented by measuring impedances between one or more electrodes, and patch electrodes attached to the skin of patient 11, such as is also provided in the Carto3® system. For simplicity, elements specific to tracking and that are used by module 154, such as the elements and patch electrodes referred to above, are not shown in FIG. 2.

Figure 3:
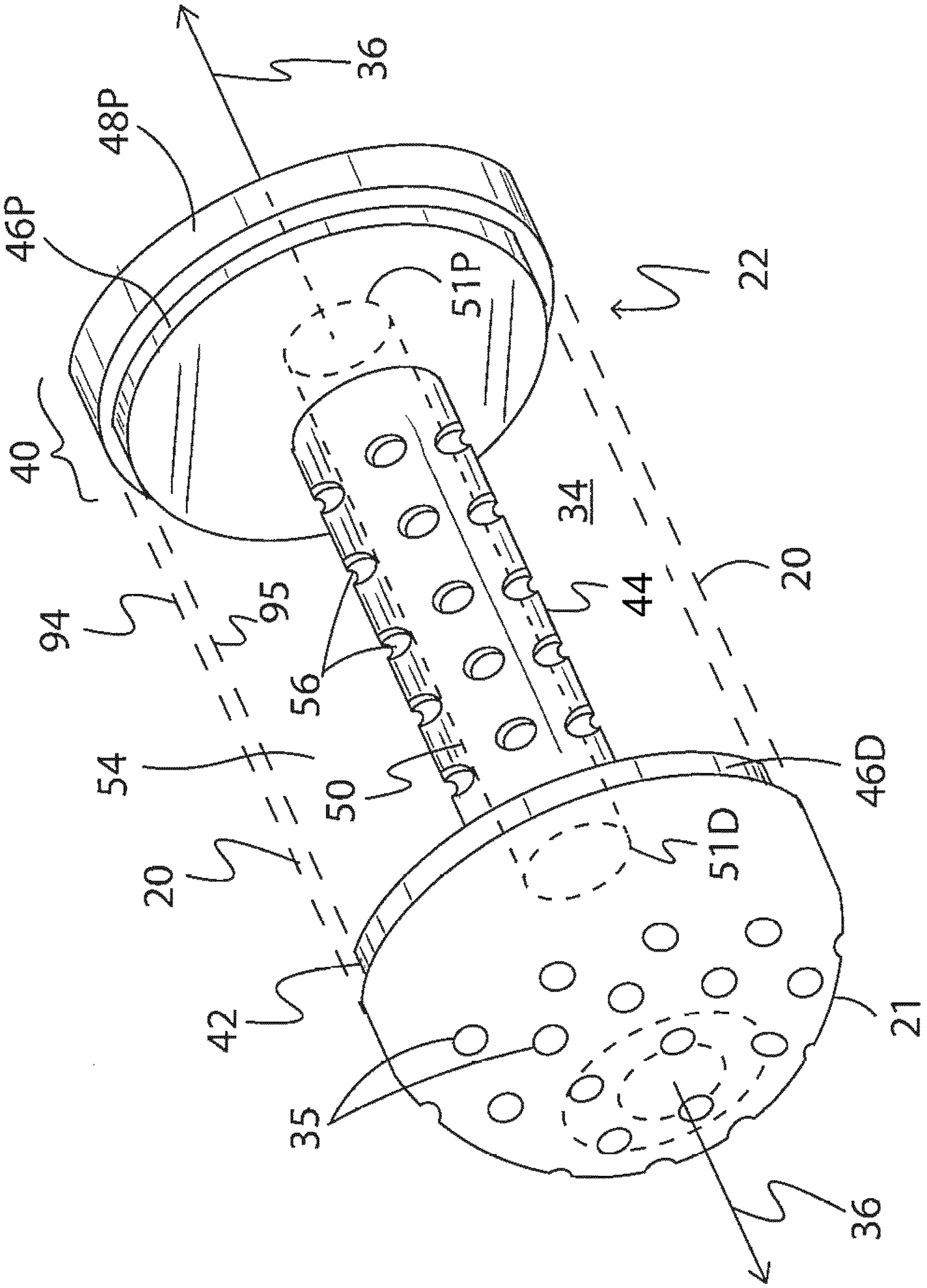
FIG. 3 is a perspective view of a support member of the distal assembly, according to an embodiment.
Figure 5A:
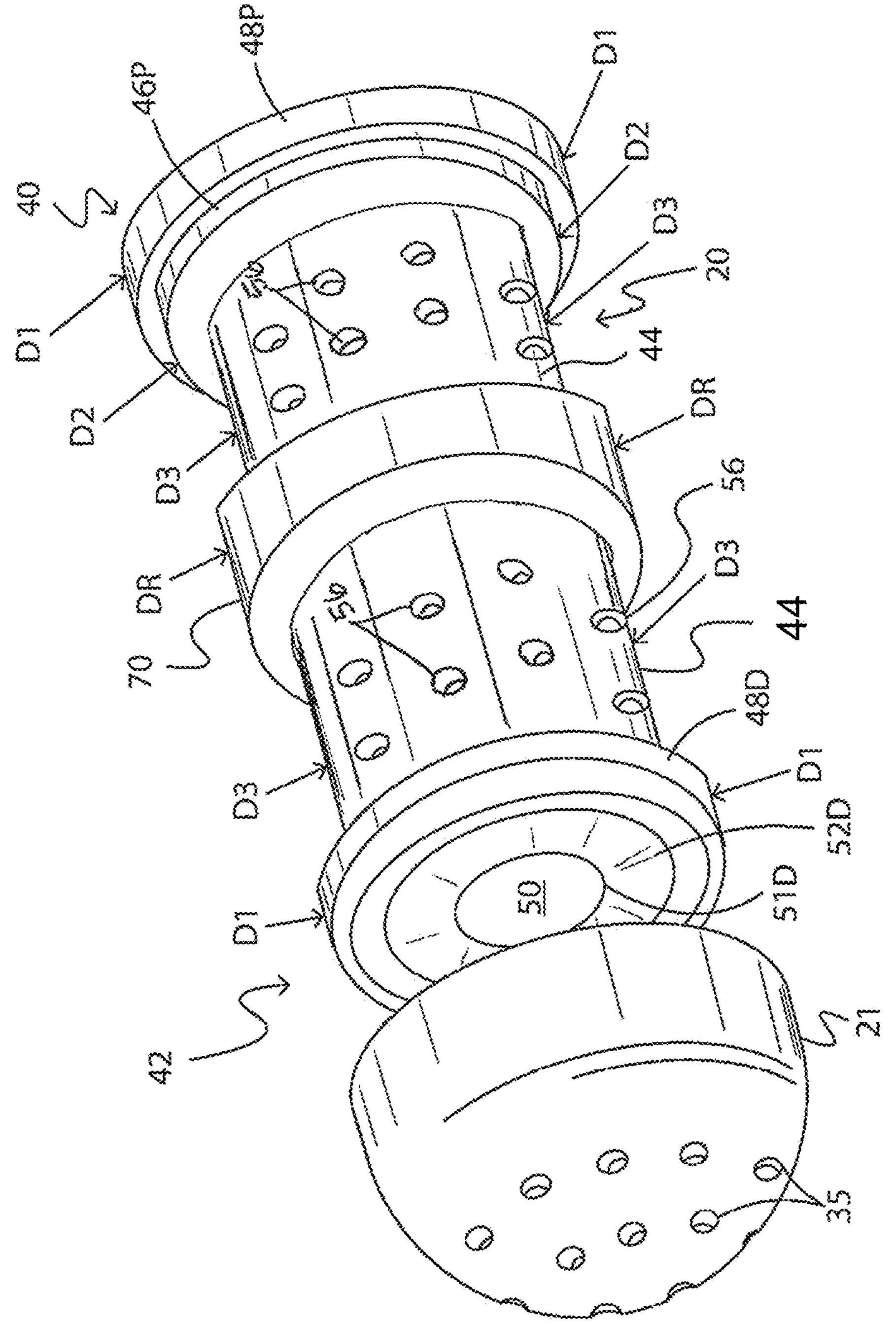
FIG. 5A is an exploded perspective view of a support member and a tip electrode of the distal assembly, according to another embodiment.

With reference to FIG. 1A, FIG. 3 and FIG. 5A, the distal assembly 15 includes a cap or a tip electrode 21, an internal support member 22, and a flex circuit 20 arranged in a generally cylindrical form on the support member 22. In some embodiments, the support member 22 may resemble a spool or a bobbin, with a proximal member or end 40, a distal member or end 42, and a longitudinal member or post 44 extending between the ends 40 and 42. The ends 40 and 42 have radial dimensions transverse to a longitudinal axis 36 of the distal assembly 15, and the post 44 is aligned and coextensive with the longitudinal axis 36. As better seen in FIG. 5A and FIG. 5B, a distal face of the distal end 42 has a recess 52D and a proximal face of the proximal end has a recess 52P to create a connection and interface between the separate distal cap 21. Each of the ends and 42 has an inner circumferential surface 46P, 46D located at a smaller diameter D1 and an outer circumferential surface 48P, 48D located at a larger diameter D2, where D1<D2, so that inner surface 95 of the proximal and distal edges 31 and 32 of the flex circuit 20 can rest on the inner circumferential surfaces 46P, 46D, respectively, and the outer tissue contact surface 94 of the flex circuit 20 can be generally flush or even with the outer diameter of the flex circuit 20. The flex circuit 20 at its proximal and distal edges 31 and 32 is affixed to these circumferential surfaces of the support member 22 by a suitable adhesive or the like.

As shown in FIG. 3 and FIG. 5A, the post 44 extends centrally through the cylindrical form of the flex circuit 20, and the post 44 itself is hollow with a longitudinal fluid channel 50 that extends through the entire longitudinal length of the member 22, from a distal opening 51D to a proximal opening 51P. Generally surrounded by the flex circuit 20, the post 44 has a radius R3 that is less than the radius R2 such than an annular space gap is provided between post 44 and the flex circuit 20, defining one or more irrigation fluid chambers 54 therebetween. A plurality of irrigation apertures 56 are formed throughout generally the entirety of the sidewall of the post 44, in all radial directions about the longitudinal axis 36, so that irrigation fluid entering the proximal opening 51P and passing through the channel 50 can exit the post 44 in any radial direction through the apertures 56 and into the one or more chambers 54. The placement, size or shape of the apertures 56 may be varied, as desired or appropriate. It is understood that the drawings do not necessarily illustrate all placement of the apertures 56 configured in the post 44—that is, apertures 56 may be configured in any surface or portion of the post 44 as desired or appropriate. Where the support member 22 is constructed of an electrically-conductive material, a lead wire (not shown) from the ablation module 150 may be connected to the support member so as to deliver energy conductively to the tip electrode 21 at the distal end of the support member for RF ablation at the tip electrode.

Figure 4A:
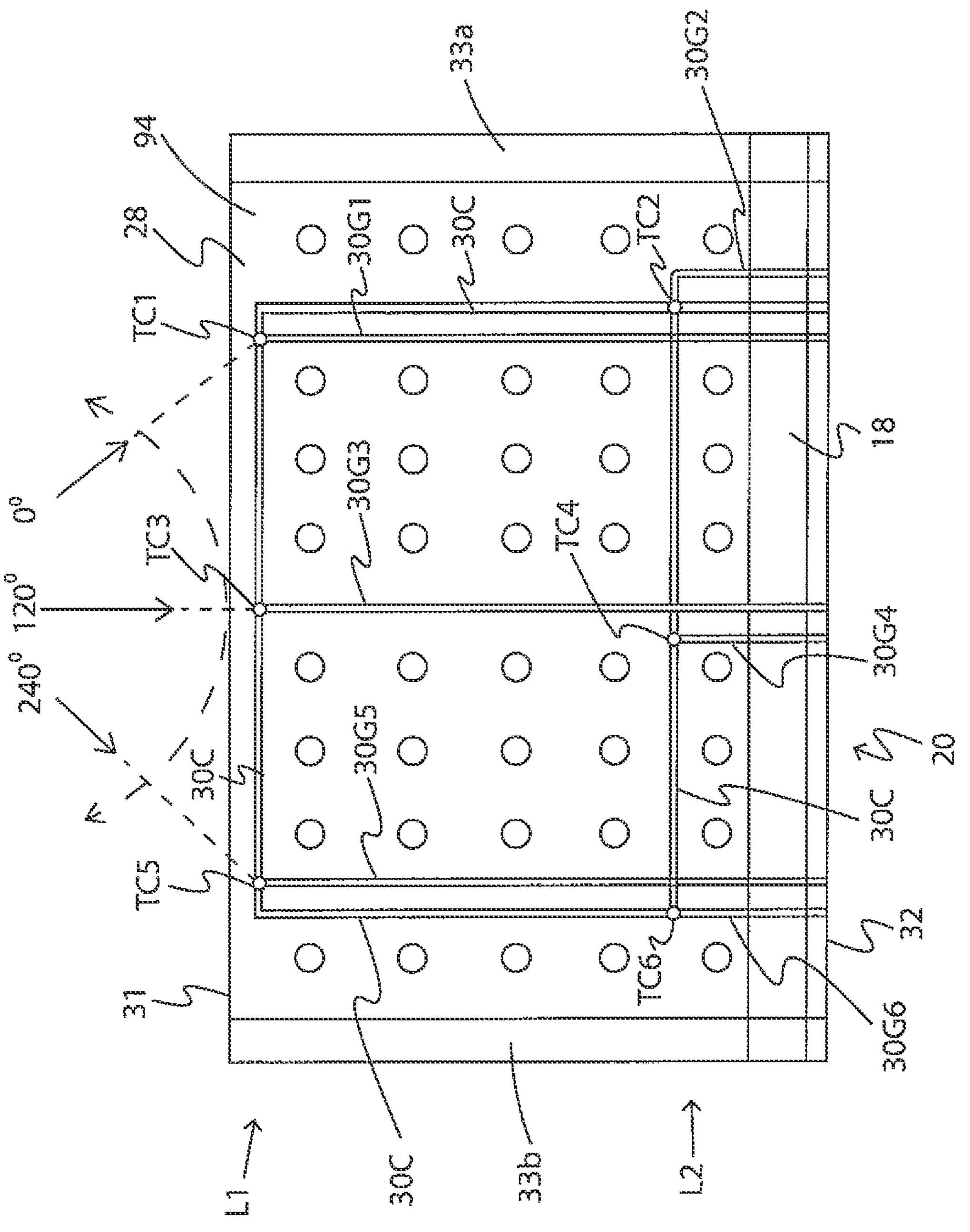
FIG. 4A is a top plan view of a flex circuit of the distal assembly, according to an embodiment.

The flex circuit 20 is rolled, wrapped or otherwise applied to portions of the support member 22 so that it forms a cylindrical shape to provide the distal assembly 15 with a circumferential tissue contact surface. In some embodiments, the flex circuit 20 has a pre-assembly configuration of a generally rectangular shape that is defined by a substrate 28 constructed of a sheet of flexible, nonelectrically-conducting, biocompatible material onto which electrically-conducting traces 30 are provided on an outer surface 94 of the substrate, as shown in FIG. 4A. (It is understood that that the terms "substrate" and "flex circuit" are used interchangeably herein, as appropriate.) The substrate 28 is configured with a distal edge 31, a proximal edge 32, and opposing side edge portions 33*a* and 33*b* that can meet, overlap and be affixed to each other, e.g., with a suitable adhesive, and to form a closed configuration, for example, a hollow cylindrical form with an interior volume 34. The cylindrical form of the flex circuit 20 as applied to the support member 22 has a center longitudinal axis that is aligned and coextensive with the longitudinal axis 36 of the distal assembly 15 such that an outer-facing surface 94 of the substrate 28 forms the circumferential tissue contact surface of the distal assembly 15.

In some embodiments, the substrate 28 is constructed of polyimide and the traces 30 include one or more trace(s) of two different metals. In the illustrated embodiment of FIG. 4A, the traces include a trace of constantan 30C and trace(s) of copper or gold 30G1, 30G2, 30G3, 30G4, 30G5 and 30G6 that are electrically isolated from each other, each serving as a distinct conductor that forms a distinct thermocouple junction TC1, TC2, TC3, TC4, TC5, and TC6, respectively, with the constantan 30C serving as the common conductor for all six junctions. The patterns of the traces, as well as the use of distinct and common conductors, may be varied as desired or appropriate. In the illustrated embodiment, each thermocouple occupies a unique position on a grid pattern on the flex circuit outer surface 94, and thus on the circumferential surface of the distal assembly 15, so that temperatures at radial angles of approximately 0, 120 and 240 degrees, along one of two different longitudinal positions L1 and L2 on the tissue contact surface of the distal assembly 15 can be sensed by the thermocouples TC1-TC6.

In some embodiments, one or more additional traces or conducting materials are provided on the substrate 28 to form one or more ring electrodes. In the illustrated embodiment of FIG. 4A, a generally linear elongated trace 30R is positioned along a proximal edge of the substrate such that it forms the ring electrode 18 on the distal assembly 15, proximal of the thermocouples TC1-TC6, when the flex circuit 20 assumes its generally cylindrical shape on the support member 20. In some embodiments, where the support member 22 is not electrically conductive, one or more additional traces 30E are provided for electrical connection to the tip electrode 21 so that electrical signals sensed by the tip electrode 21 can be passed along the catheter to the system controller 130 (FIG. 1) or energy, such as RF energy, can be delivered to the tip electrode from the ablation module 150 (FIG. 1).

The substrate 28 of the flex circuit 20 is formed generally throughout its planar sheet body with a plurality of irrigation apertures 26. The pattern and plurality may vary as desired or appropriate. The irrigation apertures 26 allow irrigation fluid to pass from the interior 34 of the generally cylindrical form on the distal assembly 15 to the outer tissue contact surface 94 of the flex circuit 20 and the tissue surrounding the distal assembly 15. The irrigation apertures 26 may have different shapes or sizes, as desired or appropriate.

In some embodiments, the flex circuit 20 is a multi-layered flexible printed circuit board (PCB) sheet having electrical interconnections, such as the conductive traces, which are configured to electrically connect electrical devices, e.g., microelectrodes, thermocouples, position sensors, and the like, coupled to the PCB to suitable wires that extend along the length of the catheter, or to other suitable circuitry. A suitable flex circuit for a distal end assembly of a catheter is described in U.S. Publication No. 2018/0110562 to Govari et al., filed Oct. 25, 2016, the entire disclosure of which is incorporated herein by reference.

Figure 4B:
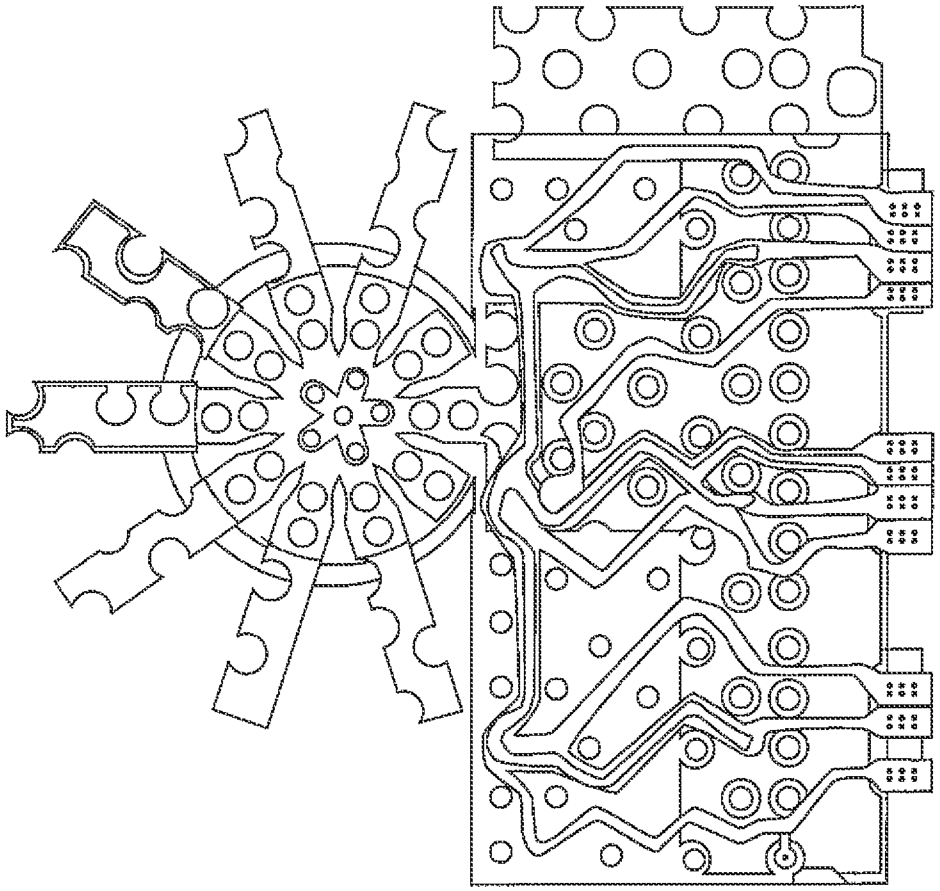
FIG. 4B is a top plan view of a flex circuit, according to another embodiment.

FIG. 4B illustrates a suitable flex circuit 200 suitable for use with a distal assembly in accordance with another embodiment. The flex circuit 200 includes a proximal portion 201 that is generally rectangular to provide the outer circumferential contact surface of the distal assembly, and a distal portion 202 to cover a tip electrode and provide a distal dome contact surface thereon. Both the portions 201 and 202 have a plurality of fluid apertures 204. The proximal portion 201 has a distal edge 201D and a proximal edge 201P, and two opposing side edges 205*a* and 205*b*, where side edge 205*b* has a side portion 206 extending laterally therefrom. The proximal portion 201 has traces, including a common trace 230 of one conductive material, e.g., constantan, and an N plurality of traces of another conductive material, e.g., copper, forming N thermocouple junctions J1-JN. In the illustrated embodiment of FIG. 4B, the flex circuit 200 has six separate traces 231-236 of the another conductive material, forming six thermocouple junctions J1-J6 with the common trace 230. In some embodiments, the outer exposed elements are the conductive surface for the delivery of RF to heat/treat the tissue, ECG electrode and ring electrode, and the inner exposed elements are a conductive surface primarily intended for thermal transfer and soldering pads to connect to the traces. All other traces such as thermocouples are located within the flex circuit. There are also connections between the various elements through various layers of the flex and terminating at the solder pads exposed on the inner surface. In some embodiments, it is preferable to configure the thermocouple junctions as close as possible to the tissue surface being measured.

The distal portion 202 is connected tangentially along a section of its distal edge to a section of the distal edge 201D of the proximal portion 201. The distal portion 202 resembles a wheel with a generally circular hub 212 and a plurality of arm portions 213 radiating outwardly like spokes from the hub.

Figure 4C:
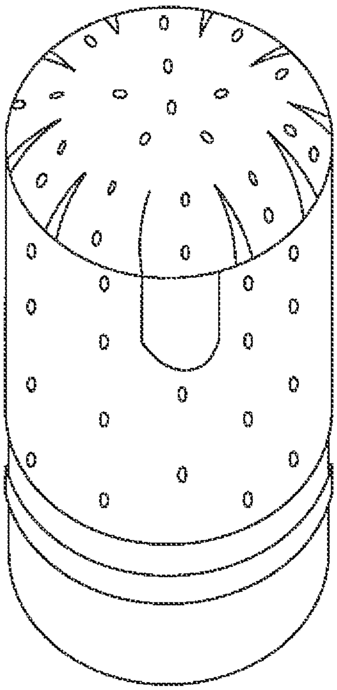
FIG. 4C is a perspective view of the flex circuit of FIG. 4B mounted on a distal assembly.

When mounting the flex circuit 200 on the distal assembly, the distal portion 202 is positioned over the tip electrode (or a member having a similar dome structure) with a center 214 of the distal portion aligned with the longitudinal axis 36, as shown in FIG. 4C. Depending on the curvature of the dome of the tip electrode, one or more folds or creases 215 are formed around the edge of the distal portion 202 to conform the distal portion 202 to the curvature. The proximal portion 201 is then wrapped circumferentially to form a cylindrical form. The arm portions 213 of the distal portion 21 are tucked under the proximal portion 201 so as to secure the distal portion 201 onto the dome. The side portion 206 is tucked under the side edge 205*a*. In that regard, the arm portions 203 and the side portion 206 have fluid apertures 204 that align with corresponding fluid apertures 204 of the proximal portion 201 so that the arm portions 203 and the side portion 206 do not obstruct the fluid apertures 204 of the portions of the proximal portion 201 overlapping the arm portions 203 and the side portion 206.

Figure 5B:
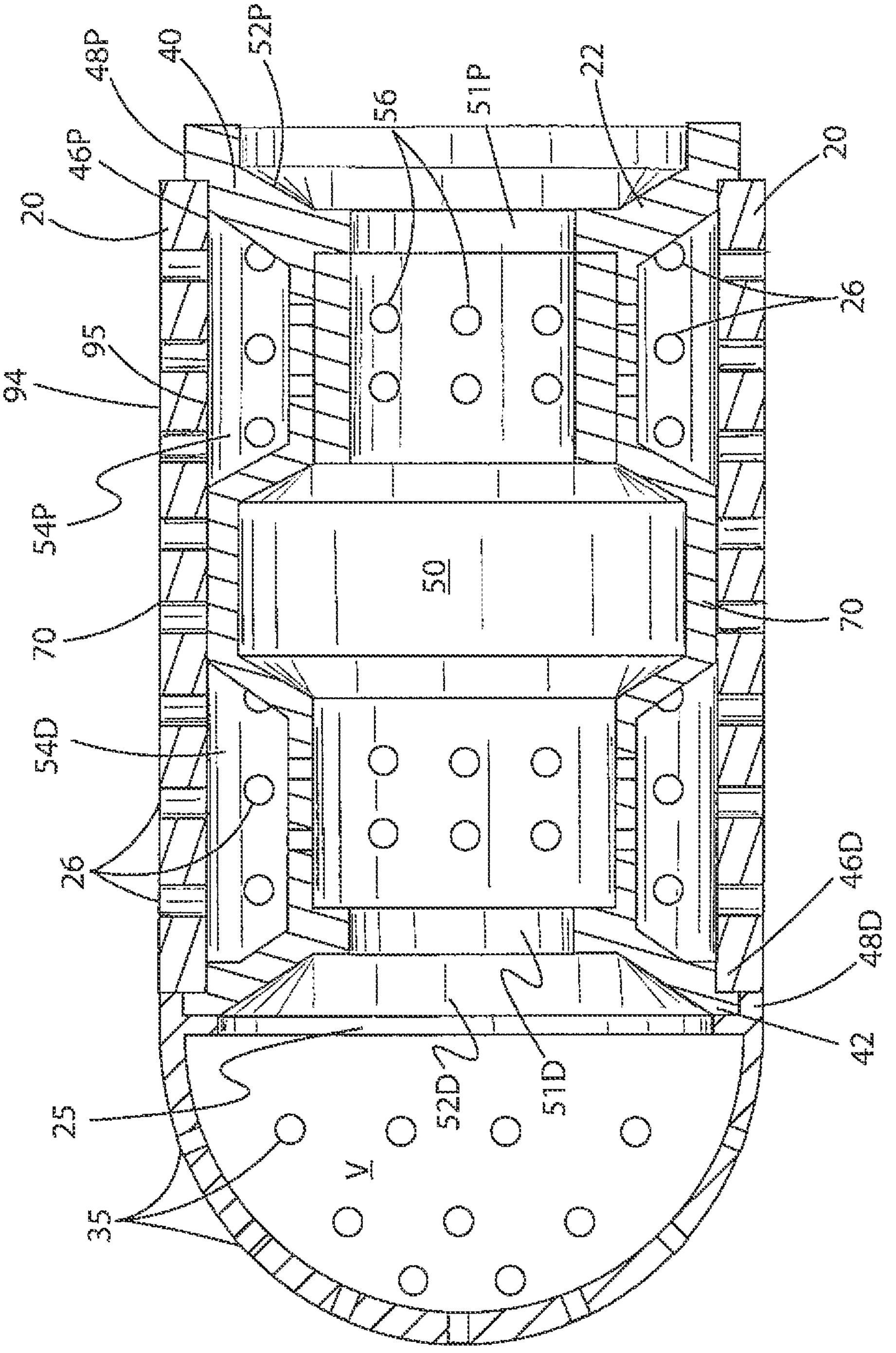
FIG. 5B is a side cross-sectional view of the support member and the tip electrode of FIG. 5A, as assembled.
Figure 9C:
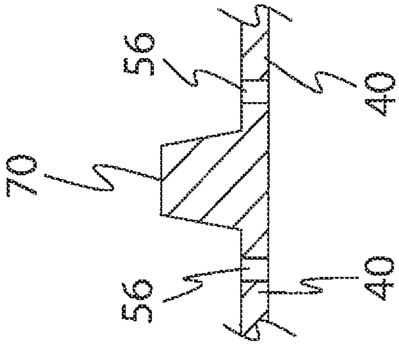
FIG. 9C is a side cross-sectional view of a raised band of a post, according to yet another embodiment.
Figure 9B:
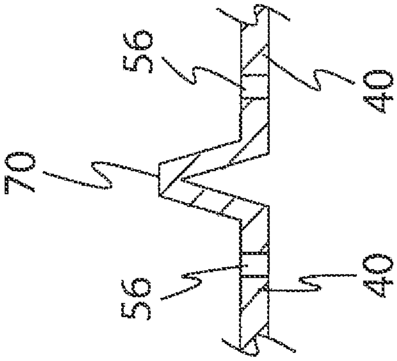
FIG. 9B is a side cross-sectional view of a raised band of a post, according to another embodiment.
Figure 9A:
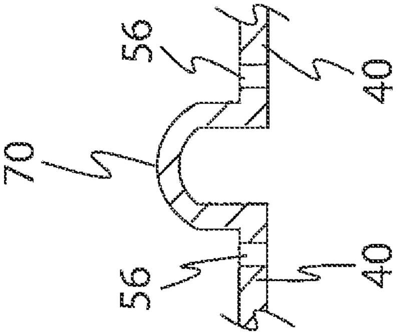
FIG. 9A is a side cross-sectional view of a raised band of a post, according to one embodiment.

With reference to FIG. 5A and FIG. 5B, in some embodiments, the sidewall 61 of the post 44 of the support member 22 is configured with one or more raised portions 70 extending outwardly in the radial direction, each extending a distance (DR/2) from the longitudinal axis 36, which is generally equally to the radius (D1/2) so that each portion 70 can contact an inner surface 95 of the flex circuit 20 and support the flex circuit 20 in its cylindrical form around the post 44. The raised portions 70 may be localized as a peak or they may span a raised area on the post 44. In the illustrated embodiment of FIG. 5A and FIG. 5B, the post 44 has a circumferential raised band 71 at about a midpoint along the length of the post. As such, the raised band 70 divide the chamber 54 into a distal chamber 54D and a proximal chamber 54P, generally of equal volume as separated by the band 70. For example, with N plurality of bands 70, N+1 plurality of separate chambers 54 can be formed within the distal assembly 15 between the post 44 and the flex circuit 20. It is understood that the width of the raised band 70 may have a different configurations The raised portion or band 70 may have a lesser width in the longitudinal direction or have a different cross-sectional shape, e.g., U-shape (FIG. 9A), V-shape (FIG. 9B), or a solid shape (FIG. 9C).

Figure 6A:
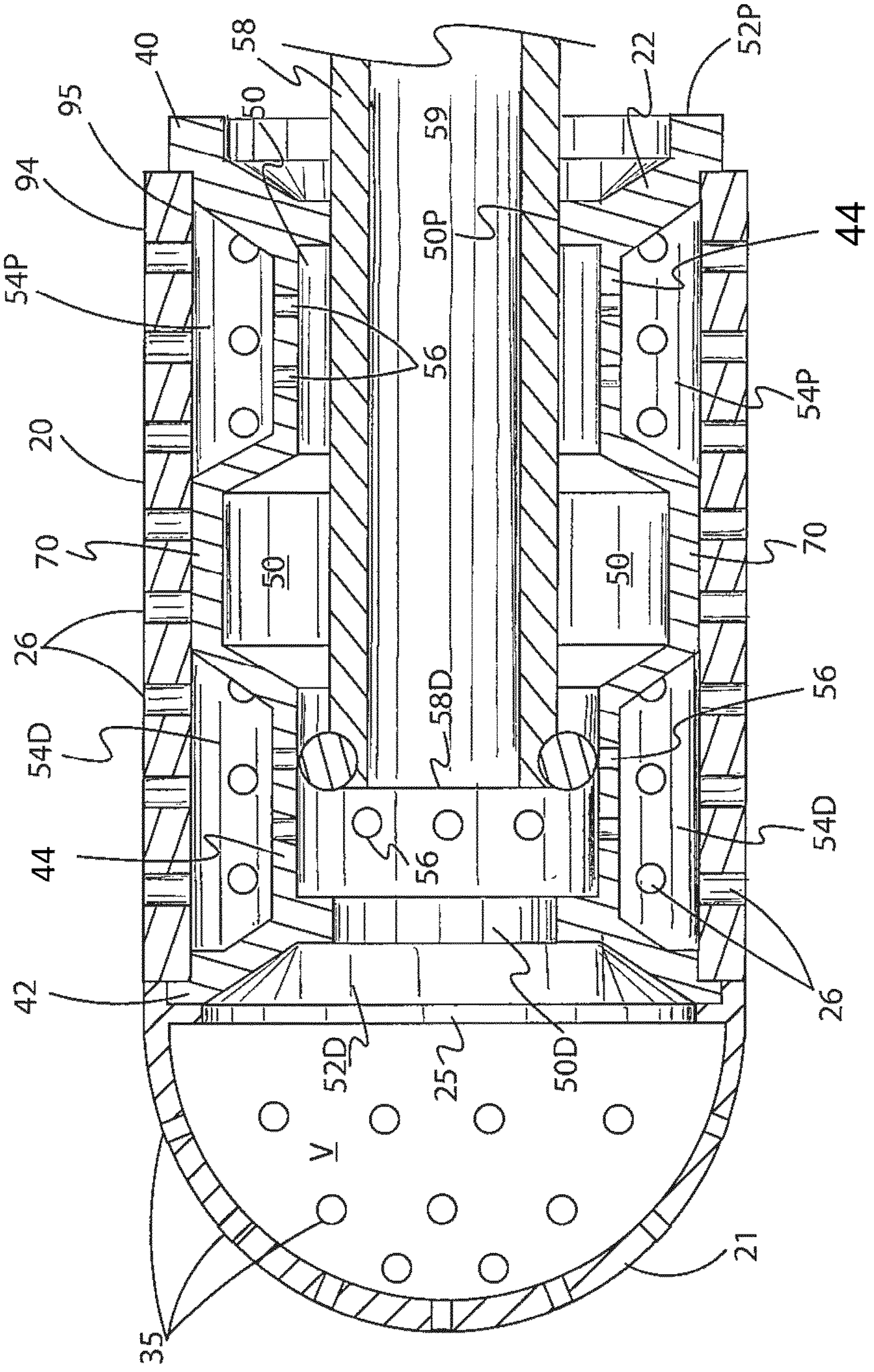
FIG. 6A is a side cross-sectional view of the support member and the tip electrode of FIG. 5B, with a flow director in a more distal position.
Figure 6B:
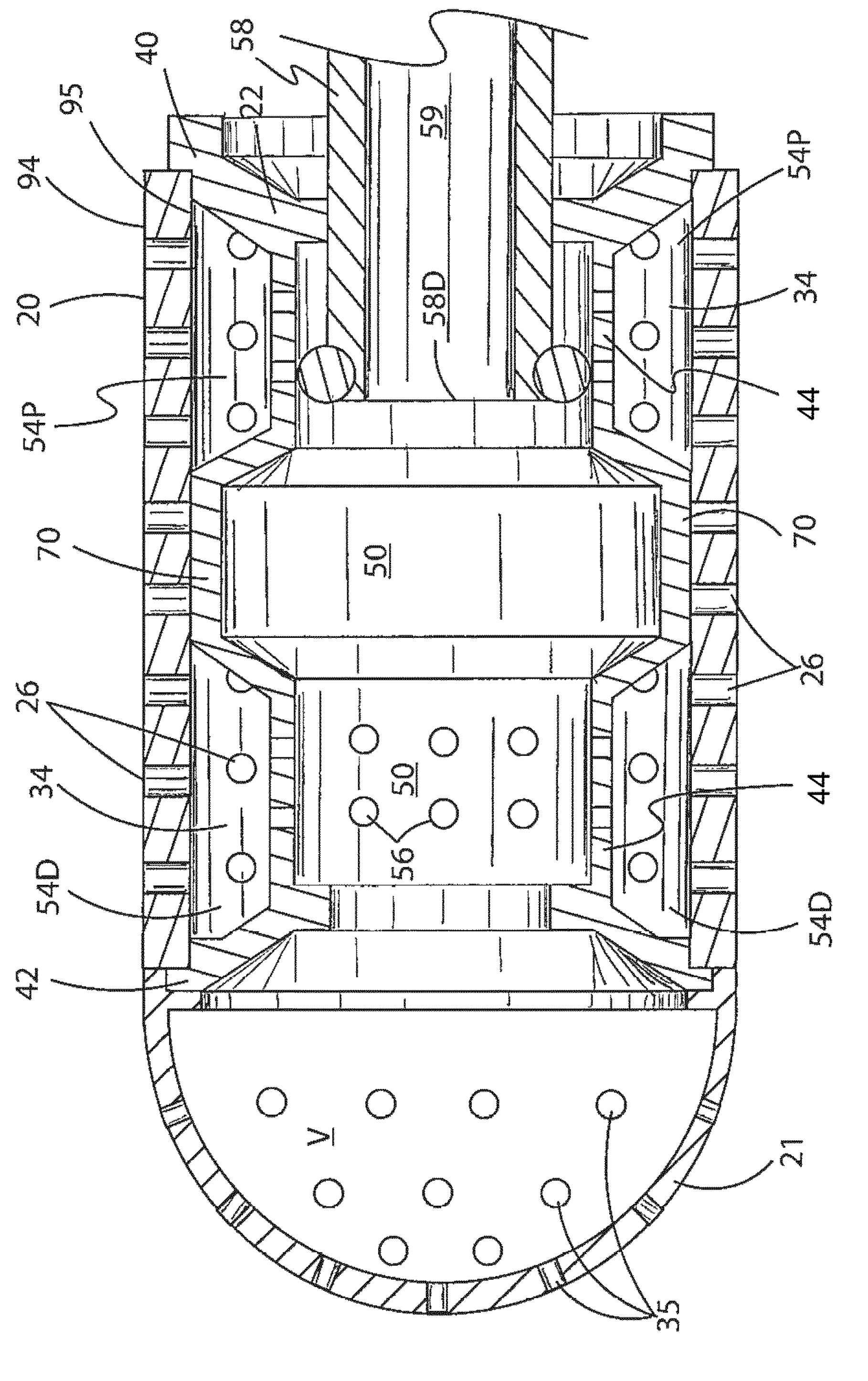
FIG. 6B is a side cross-sectional view of the support member and the tip electrode of FIG. 5B, with the flow director in a more proximal position.

As shown in FIG. 6A and FIG. 6B, in some embodiments, the support member 22 includes a flow director 58 that is movable within the channel 50 in the post 44. In some embodiments, the flow director 58 may be a tubing with a lumen 59 through which irrigation fluid can pass distally from a proximal end and exit via a distal opening 58D. The flow director 58 is sized and configured for longitudinal movement within the channel 50 relative to the support member 22 such that the operator 19 can manipulate the flow director 58 to position the distal opening 58D at a selected location within the channel 50 of post 44 and direct irrigation fluid to selected portions and chambers within the distal assembly 15. An O-ring 91 may be provided, for example, at or near a distal end of the flow director 58 to provide a fluid-tight seal around a distal end of the flow director.

In some embodiments, the system controller 130, the irrigation module 152, and the temperature sensing module 156 (FIG. 1) can be configured to control and manipulate the flow director 58. For example, the flow director 58 can be coupled to an actuator responsive to the system controller 130 to adjust movement of the flow director 58 along longitudinal axis 36 between a more distal position (FIG. 6A) in the support member 22 where sidewall 61 of the post 44 blocks and seals off those irrigation apertures 56 proximal of the distal opening 58D, and a more proximal position (FIG. 6B) where the sidewall 61 of the post 44 leaves more irrigation apertures 56 unblocked and open allowing additional irrigation fluid volume to be delivered out of the body 20. Depending on the position of the flow director 58, the irrigation fluid can be delivered by the flow director 58 from its lumen 59 to different parts of the channel 50 and into one or more chambers 54. For example, where cooling is desired in all regions of flex circuit 22, the flow director 58 can be positioned more proximally in the channel 50 for larger volume of fluid circulation. For example, where more cooling is desired in a distal region of the flex circuit 22, the flow director 58 can be positioned more distally in the channel 50. Moreover, where more cooling is desired in the tip electrode 21, the flow director 58 can be positioned in a distal-most position where the post 44 blocks off all irrigation apertures 56 in the channel 50 of the post 44 so that all irrigation fluid is directed into the tip electrode 21. The flow director 58 can therefore be manipulated by an operator to control the cooling of the distal assembly 15, including the tip electrode 21, by allowing adjustment of its position longitudinally relative to the support member 22 and the distal assembly 15, whereby longitudinal movement of the flow director 58 proportionally controls the cooling rate of the distal assembly 15.

The tip electrode 21 is configured as an atraumatic dome with a thin shell S and is suitable for tissue contact in sensing electrical activity or delivery energy, including RF energy, for ablation with tissue contact. In some embodiments, the tip electrode 21 is mounted on a distal end of the support member 22, where the tip electrode 21 has a circumferential flange 23 that receives and surrounds a distal end of the support member 22. In some embodiments, the tip electrode 21 is electrically energized via the flex circuit 20. In some embodiments, the tip electrode 21 is electrically energized by energy conducted via the support member 22 which is energized via a lead wire (not shown) that passes through the length of the catheter, as known in the art. In some embodiments, the tip electrode 21 may be constructed in its entirety of one or more metallic materials. In some embodiments, the tip electrode 21 is constructed of a metallized material, for example, with a nonmetallic material as a base and a metallic outer layer, such as an electrically-conductive outer coating or deposit, such as of gold. The tip electrode may also carry a flex circuit on its outer distal surface. In some embodiments, the dome 21 is metallic. In some embodiments, the dome 21 is plated plastic. In some embodiments, the dome 21 includes a formed flex circuit with a metalized outer surface with internal thermocouple junctions.

As shown in illustrated embodiments of FIG. 6A and FIG. 6B, the tip electrode 21 has a proximal opening 25 that leads to an interior volume V configured to receive irrigation fluid. In some embodiments, the opening 25 is defined by a radial flange 27 within the circumferential flange 23, where the radial flange 27 abuts with the distal end of the support member 22. The thin-walled, dome shell S may be formed by stamping and is provided with a plurality of irrigation apertures 35 generally throughout the shell so that irrigation fluid entering the interior volume V can exit to outside of all regions of the shell S.

The tip electrode 21, the internal support member 22 and the flex circuit 20 are configured to allow ease of assembly via manual labor or robotics automation. Additionally, the construction material of the tip electrode 21 or the support member 22 may be a thermally-conductive metallic material, or a combination of thermally-conductive and thermally-nonconductive material, or the like. In some embodiments, the support member 22 can be manufactured out of a biocompatible plastic via micro-injection molding.

Figure 7:
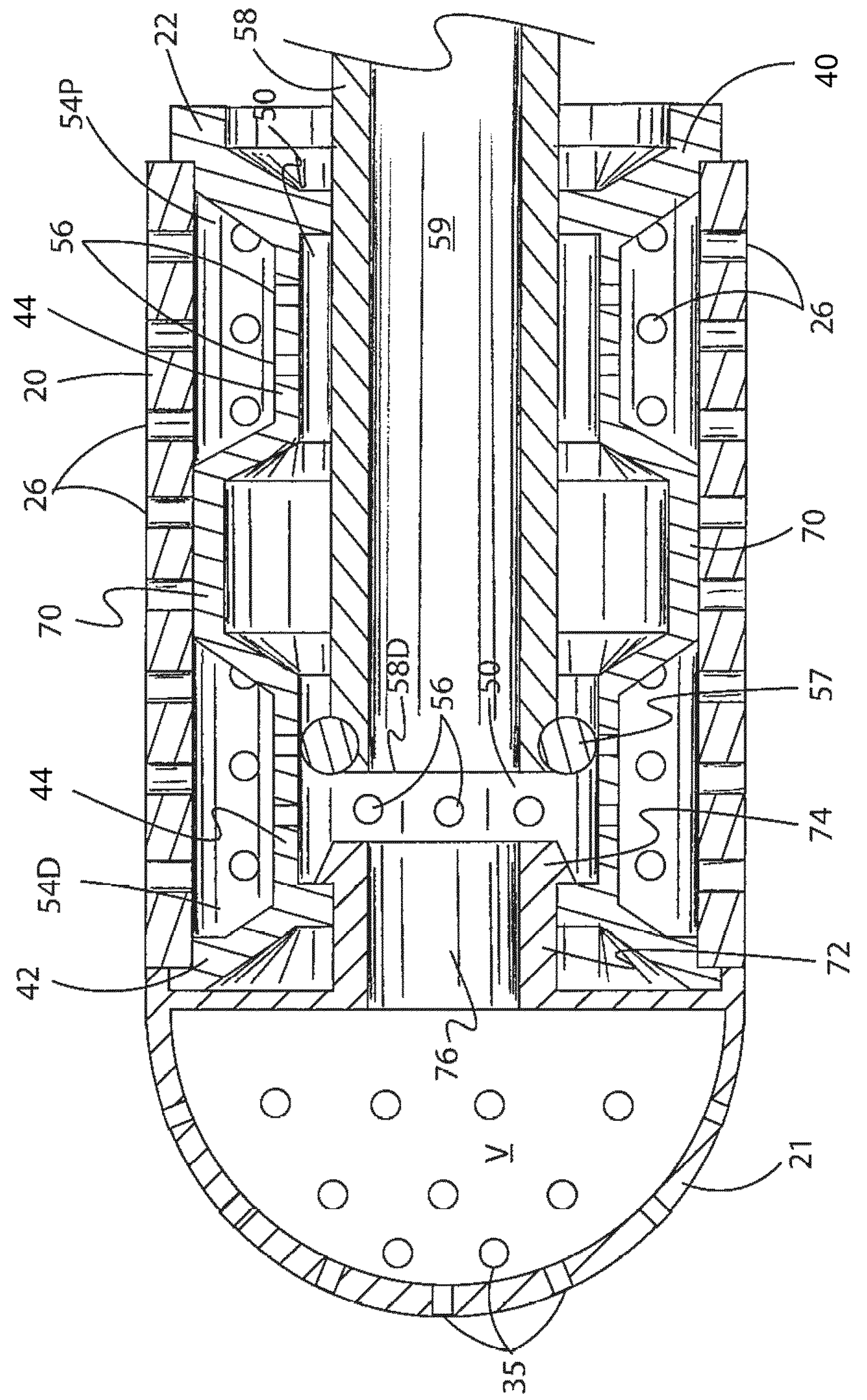
FIG. 7 is a side cross-sectional view of a support member and a tip electrode, according to yet another embodiment.

The tip electrode 21 can be readily mounted on the distal end of the internal support member 22 using an interference fit and affixation by a suitable adhesive. To that end, the tip electrode 21 in some embodiments, as illustrated in FIG. 7, has a male coupler 72 that extends along the longitudinal axis 36 and is received in the distal opening 51D of the channel 50 in the support member 22. The male coupler 72 has a lip 74 that catches on a rim of the distal opening 51D to secure against detachment. The male coupler 72 has a longitudinal lumen 76 to allow irrigation fluid to pass from the internal support member 22 into the interior volume V. Moreover, the lumen 76 is in alignment with and sized comparable to the lumen 59 of the flow director 58 so that irrigation fluid can flow directly from the lumen 59 into the lumen 76 when the flow director 58 is in its distal-most position. It is understood that in some embodiments, the distal end of the support member 22 has a male coupler that is received in a female coupler of the tip electrode 21. It is also understood that the tip electrode 21 has a generally solid construction with irrigation pathways that extend through the solid construction and provide fluid communication between the chamber(s) 54 and outside the tip electrode.

In some embodiments, the distal assembly 15 includes a force sensor 80 whose distal end is connected to the proximal end of the internal support member 22. Aspects of a force sensor similar to force sensor 58 are described in U.S. Pat. No. 8,357,152, to Govari et al., issued Jan. 22, 2013, and in U.S. Patent Publication 2011/0130648, to Beeckler et al., filed Nov. 30, 2009, both of whose disclosures are incorporated herein by reference. With reference to FIG. 1A, the force sensor 80 comprises a resilient coupling member 81, which forms a spring joint between two ends of the coupling member. In some embodiments, the coupling member 81 is understood to be formed in two parts or having a first or distal assembly 81D and a second or proximal portion 81P, the two portions being fixedly joined together. The two portions of coupling member 81 are generally tubular, and are joined so that the coupling member also has a tubular form with a central lumen 82 therethrough. In the embodiments where the coupling member 81 is formed of two portions, the two portions implementation simplifies assembly of elements comprised in the force sensor, as well as of other elements mounted in the distal end, into the member 81.

The coupling member 81 typically has one or more helices 83 cut or otherwise formed in a section of the length of distal assembly 81D, so that the member behaves as a spring. In an embodiment described herein, and illustrated in FIG. 1A, helices 83 are formed as two intertwined helices, a first cut helix 83A and a second cut helix 83B, which are also referred to herein as a double helix. However, coupling member 81 may have any positive integral number of helices, and those having ordinary skill in the art will be able to adapt the present description without undue experimentation to encompass numbers of helices other than two. Alternatively, the coupling member may comprise a coil spring or any other suitable sort of resilient component with similar flexibility and strength characteristics to those generated by the one or more tubular helical cuts, referred to above.

The coupling member 81 is mounted within and covered by a nonconducting, biocompatible sheath 84, which is typically formed from flexible plastic material. Coupling member 81 typically has an outer diameter that is approximately equal to the inner diameter of sheath 84. Such a configuration, having the outer diameter of the coupling member to be as large as possible, typically increases the sensitivity of force sensor 80. In addition, and as explained below, the relatively large diameter of the tubular coupling member, and its relatively thin walls, provide the relatively spacious central lumen 82 enclosed within the coupling member which can be occupied by other elements.

When catheter 10 is used, for example, in ablating endocardial tissue by delivering RF electrical energy through electrode 21 or electrode 18, considerable heat may be generated in the distal assembly 15. For this reason, it is desirable that sheath 84 comprises a heat-resistant plastic material, such as polyurethane, whose shape and elasticity are not substantially affected by exposure to the heat.

Within force sensor 80, typically within the central lumen 82 of the coupling member 81, a joint sensing assembly, comprising coils 86, 87, 88 and 89, provides accurate reading of any dimensional change in the spring joint of the force sensor 80, including axial displacement and angular deflection of the joint. These coils are one type of magnetic transducer that may be used in embodiments of the present invention. A "magnetic transducer," in the context of the present patent application and in the claims, means a device that generates a magnetic field in response to an applied electrical current or outputs an electrical signal in response to an applied magnetic field. Although the embodiments described herein use coils as magnetic transducers, other types of magnetic transducers may be used in alternative embodiments, as will be apparent to those skilled in the art.

The coils in the sensing assembly are divided between two subassemblies on opposite sides of spring joint: one subassembly in one portion (e.g., distal assembly 81D) of the member 81 comprises coil 86, which is driven by a current, via a cable (not shown) from the system controller 130 and the force module 148, to generate a magnetic field. This field is received by a second subassembly, comprising coils 87, 88 and 89, which are located in another portion (e.g., proximal portion 81P) of the member 81, opposing the coil 86 from across the helice(s) 83. Coils 87, 88 and 89 are fixed in distal end 12 at different radial locations about the longitudinal axis 36. Specifically, in this embodiment, coils 87 88 and 89 are all located in the same plane perpendicular to the axis 36, at different azimuthal angles about the longitudinal axis 36, and have respective axes of symmetry generally parallel to axis 364. For example, the three coils may be spaced azimuthally 120° apart at the same radial distance from the longitudinal axis 36.

Coils 87, 88 and 89 generate electrical signals in response to the magnetic field transmitted by the coil 86. These signals are conveyed by a cable (not shown) to the system controller 130, which uses the force module 148 to process the signals in order to measure the displacement of spring joint parallel to axis 36, as well as to measure the angular deflection of the joint from the axis. From the measured displacement and deflection, the system controller 130 is able to evaluate, typically using a previously determined calibration table stored in force module 148, a magnitude and a direction of the force on the spring joint of the coupling member 81. In some embodiments, a second ring electrode 93 is carried on the proximal portion 81P.

The system controller 130 uses the tracking module 154 (FIG. 1) to measure and detect the location and orientation of distal end 12. The method of detection may be by any convenient process known in the art. In some embodiments, magnetic fields generated external to patient 11 (e.g., by generators positioned below patient's bed) generate electric signals in a position sensor 90 housed in the proximal portion 81P. As shown in FIG. 1B, the position sensor 90 comprises sensing coil X, coil Y, and coil Z (which in some embodiments is one of the coils 87, 88 and 89). The system controller 130 processes the electric signal to evaluate the location and orientation of the distal assembly 15. Alternatively, the magnetic fields may be generated in the distal assembly 15, and the electrical signals created by the fields may be measured external to patient 11.

The irrigation fluid is delivered to distal assembly 15 by an irrigation tubing 91 with lumen 92. The irrigation tubing 91 extends through the deflection section 14 and the catheter shaft 12. A distal end of the irrigation tubing 91 is coupled to a proximal end of the flow director 58 such that the lumen 92 is in communication with the lumen 59 of the flow director 58. In some embodiments, the irrigation tubing 91 at its proximal portion extends past the control handle 16 such that a proximal end is exposed so that the operator can manipulate the irrigation tubing 91 by pulling or pushing the flow director 58 in a more proximal position or a more distal position in the support member 22 in directing flow of the irrigation fluid. In some embodiments, the system controller 130 is configured to actuate movement of the irrigation tubing 91 in response to the temperature sensing module 156. In some embodiments, the irrigation tubing 91 is integral with and a proximal portion of the flow director 58. In some embodiments, the irrigation fluid is a saline solution, and the rate of flow of the fluid, controlled by the irrigation module 52.

Figure 8A:
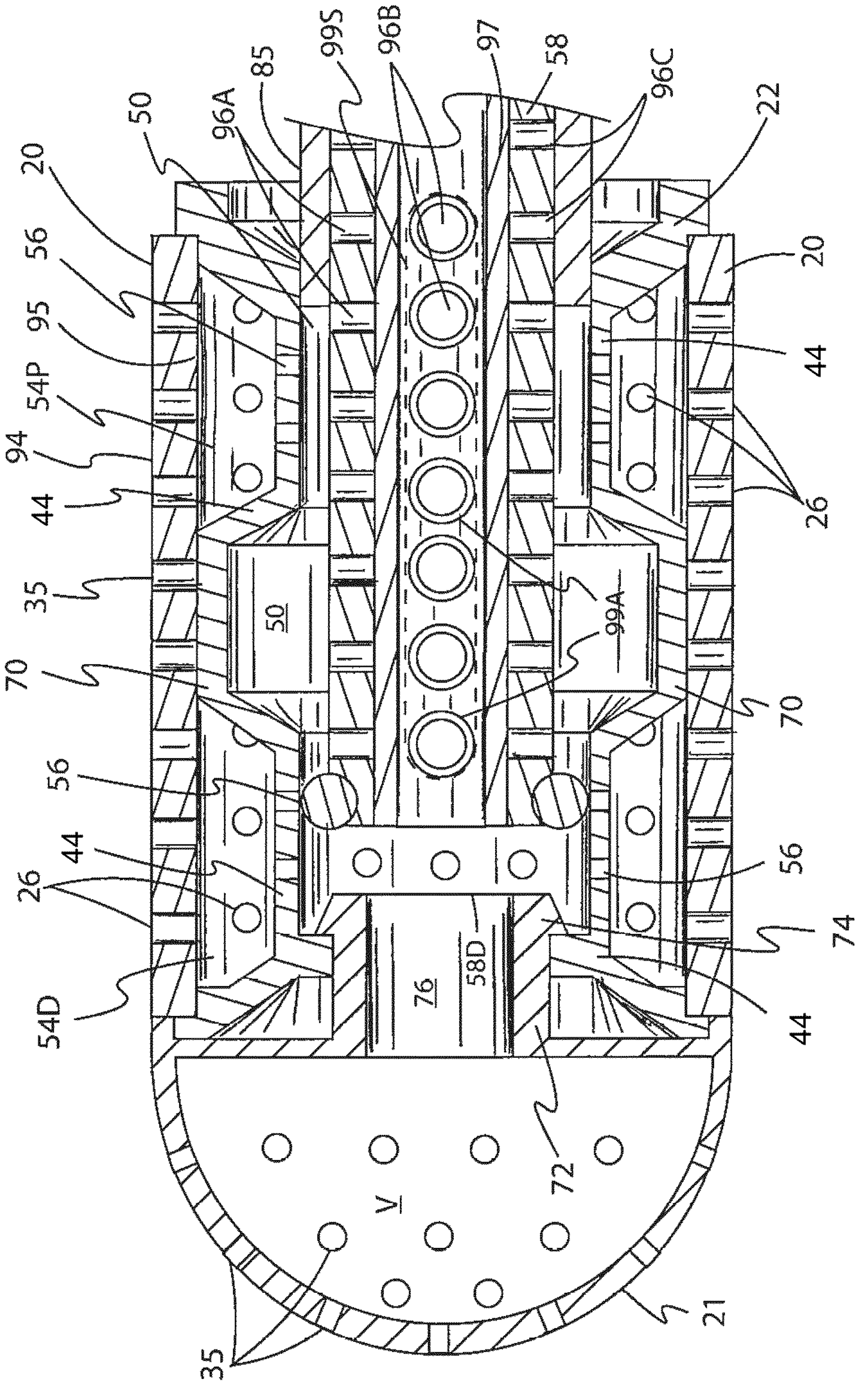
FIG. 8A is a side cross-sectional view of a support member, a first or outer flow director and a second or inner flow director, according to yet a further embodiment, with the second flow director in one radial position.
Figure 8B:
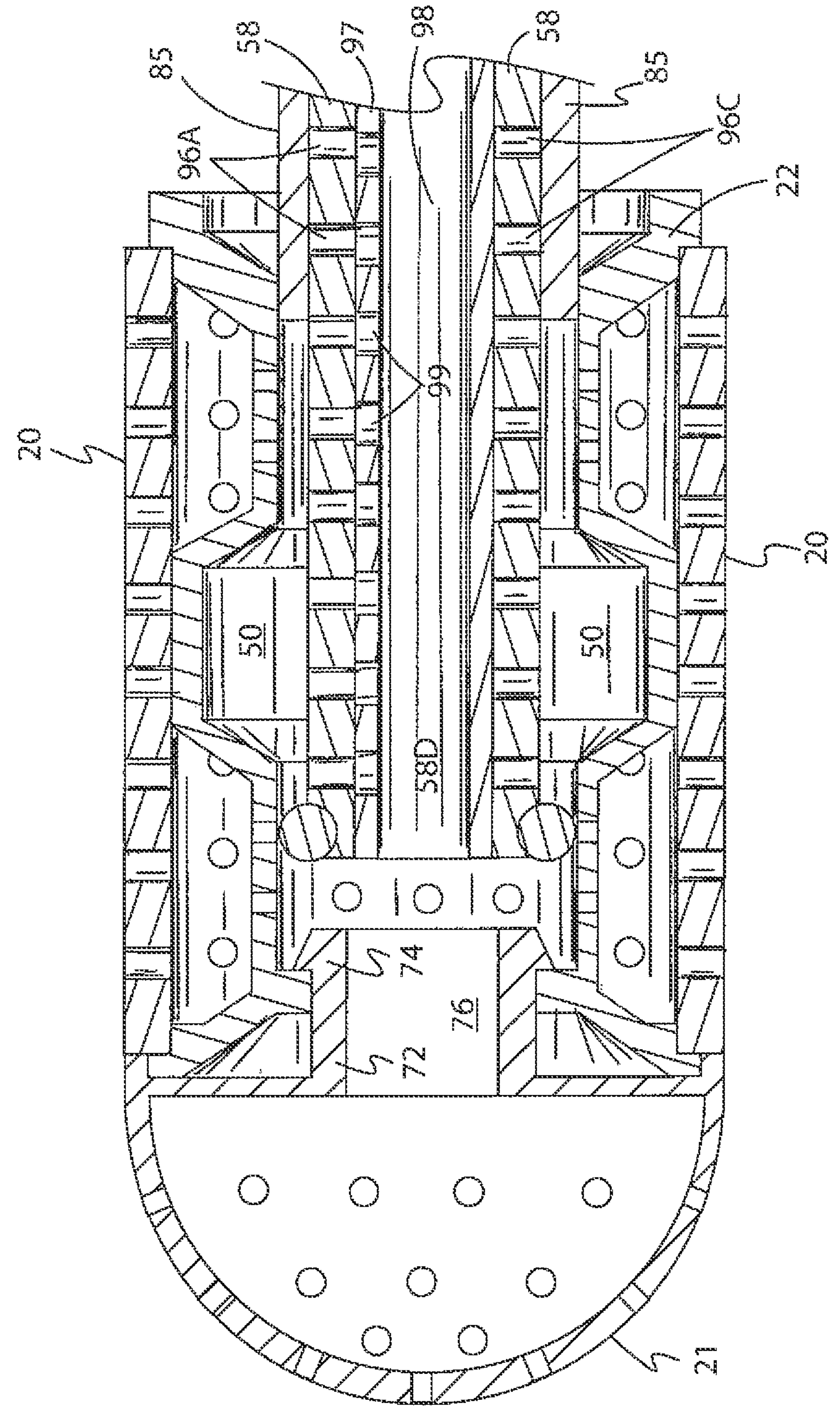
FIG. 8B is a side cross-sectional view of the support member, the first or outer flow director and the second or inner flow director of FIG. 8A, with the second flow director in another radial position.

In some embodiments, as shown in FIG. 8A, a distal portion of the sidewall of the flow director 58 that can extend inside the support member 22 has irrigation apertures 96 in generally all radial directions about the longitudinal axis 36, e.g., 96A, 96B, 96C as shown. A second or inner flow director 97, e.g., a tubing with lumen 98, is nested in the lumen 59 of the flow director 58. A sidewall in the distal portion of the second flow director 97 that can extend within the support member 22 has an irrigation formation 99, e.g., longitudinal slot 99S (in broken lines) or longitudinally-arranged irrigation apertures 99A (in solid lines), that can be aligned with a longitudinal group of irrigation apertures 96 when the second flow director 97 is rotated along its longitudinal axis by the operator 19 or the system controller 130. In the illustrated embodiment of FIG. 8A, the second flow director 97 has been rotated so that the irrigation formation 99 is aligned with the apertures 96B so that there is fluid communication therebetween and irrigation fluid is directed to exit the post 44 via the apertures 96B. However, as shown in FIG. 8B, the second flow director 97 has been rotated so that its irrigation formation 99 is aligned with the apertures 96A so that there is fluid communication therebetween and irrigation fluid is directed to exit the post 44 via the apertures 96A. The second flow director 97 thus enables radial directional control in the flow of irrigation fluid about the longitudinal axis 36 within the distal assembly 15. An outer tubing 85 is provided to circumferentially surround the exposed proximal portion of first or outer flow director 58.

Means for irrigating the distal assembly 15 are shown and described in one of many examples in relation to the post 44 of the support member 22, the first flow director 58 and the second flow director 97, as shown in FIG. 3, FIG. 5A, FIG. 5B, FIG. 6A, FIG. 8A and FIG. 8B, including equivalents thereof as well as those provided by later developed technologies.

In use, the catheter 10 is introduced into the patient's vascular system and the distal assembly 15 is advanced to an area of interest, for example, a heart chamber. The system controller 130 accomplishes diagnostic procedures, including mapping. For example, the position sensor 90 generates signals processed by the tracking module 154 in determining location and orientation of the distal assembly 15. The tip electrode 21, the distal ring electrode 18 or the proximal ring electrode 93 sense electrical activity of adjacent heart tissue which signals generated are processed by processing unit 132. A 3-D electrophysiology map may be created from these processed signals, and ablation tissue sites are identified and targeted. The system controller 130 may then accomplish therapeutic procedures. For example, the operator maneuvers the distal assembly 15 so that the tip electrode 21 is in contact with the targeted tissue site. Contact between the tip electrode 21 and tissue results in the application of a force that displaces the distal assembly 81D relative to the proximal portion 81P of the force sensor 148. Such displacement causes the coils 87, 88 or 89 to generate signals that are processed by the force module 148, for example, to confirm contact of the distal assembly 15 and tissue in preparation for ablation.

Before or during ablation, the irrigation module 152 controls delivery and rate of delivery of irrigation fluid to the distal assembly 15 by a pump (not shown) that delivers irrigation fluid from a fluid source (not shown) through the lumen 92 of the irrigation tubing 91 and the lumen 59 of the flow director 58 (which in some embodiments may include the irrigation tubing 91 as its proximal portion). The flow director 58 is positioned by an operator or the system controller 130 such that its distal opening 58D is, for example, in a more proximal position. The ablation module 150 delivers RF energy to the tip electrode 21 which heats the target tissue to form a lesion. One or more of the thermocouples TC1-TC6 generate signals representative of temperature of respective surrounding tissue and fluids. Depending on the temperature(s) sensed, the system controller 130 may in some embodiments communicate with the ablation module 150 to adjust the power delivery or with the irrigation module 152 to adjust the rate of fluid delivery or the position of the flow director 58 to its distal-most position, a more distal position or a less proximal position, as appropriate to avoid hot-spots, charring or thrombosis. Irrigation fluid can therefore be directed to flow out in various manners, including, e.g., (i) all the irrigation apertures 35, 56 and 26, (ii) all of the irrigation apertures 35 and a portion of the irrigation apertures 56, or (iii) solely the irrigation apertures. Additionally, where the catheter 10 includes a flow director 58 with irrigation apertures 96, and a second flow director 97 with a radially-directed slot 99S or irrigation apertures 99A, the operator or the system controller 130 can also manipulate the second flow director 97 to control a radial direction of irrigation fluid flow. In that regard, the longitudinal formation 99, e.g., the slot 99S and the apertures 99A, may be larger or wider than the apertures 96 to facilitate fluid communication between them.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention, and that the drawings are not necessarily to scale. Moreover, it is understood that any one feature of an embodiment may be used in lieu of or in addition to feature(s) of other embodiments. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter comprising:

an elongated shaft; and a distal assembly, including:

a tip electrode with a proximal end configured with a first coupler;

a support member with a longitudinal axis and a distal end, the distal end configured with a second coupler coupled to the first coupler, the support member including a distal member with a proximal circumferential edge defining a first radius, a proximal member with a distal circumferential edge defining a second radius, and a post extending longitudinally and connecting the distal member and the proximal member, the post defining a third radius generally equal to the first and second radii;

a flex circuit circumferentially surrounding the support member; and at least one internal irrigation chamber between the support member and the flex circuit.

2. The catheter of claim 1, wherein the first coupler includes a lip and the second coupler includes a rim.

3. The catheter of claim 1, wherein the flex circuit includes a generally rectangular portion extending circumferentially around the support member.

4. The catheter of claim 1, wherein the first coupler includes a male coupler and the second coupler includes a female coupler.

5. The catheter of claim 1, wherein the first coupler includes a female coupler and the second coupler includes a male coupler.

6. The catheter of claim 1, wherein the flex circuit is supported circumferentially around the support member by a first circumferential edge of the distal member and a second outer circumferential edge of the proximal member.

7. The catheter of claim 1, wherein the post of the support member includes a fluid channel extending along the longitudinal axis.

8. The catheter of claim 7, wherein the post is configured with irrigation apertures.

9. The catheter of claim 8, wherein the flex circuit is configured with irrigation apertures.

10. A catheter comprising:

an elongated shaft; and a distal assembly, including:

a support member defining a longitudinal axis, the support member configured with an irrigation channel extending along the longitudinal axis; and an outer flow director and an inner flow director concentrically arranged with each other and both configured for longitudinal movement within the irrigation channel relative to the support member, the outer flow director configured with first irrigation apertures and the inner flow director configured with an irrigation formation, the inner flow director configured for radial rotation relative to the outer flow director; and a flex circuit surrounding the support member circumferentially, the flex circuit configured with second irrigation apertures.

11. The catheter of claim 10, wherein the irrigation formation of the inner flow director includes a longitudinal slot.

12. The catheter of claim 10, wherein the irrigation formation of the inner flow director includes third irrigation apertures.

13. The catheter of claim 10, wherein the first irrigation apertures of the outer flow director are arranged in multiple radial directions configured for alignment with the irrigation formation of the inner flow director depending on a rotational position of the inner flow director relative to the outer flow director.

14. The catheter of claim 10, wherein the support member includes a distal member, a proximal member, and a post extending therebetween, the irrigation channel extending through the post.

15. The catheter of claim 14, wherein the flex circuit is in contact with the distal member and the proximal member of the support member.

16. The catheter of claim 14, wherein the post of the support member includes a raised portion between the distal member and the proximal member, and the flex circuit is in contact with the distal member, the proximal member and the raised portion.

17. The catheter of claim 10, wherein the distal assembly includes a tip electrode configured with an interior volume and tip irrigation apertures, and a distal end of the irrigation channel is in fluid communication with the interior volume of the tip electrode.

18. The catheter of claim 10, wherein the distal assembly includes an o-ring extending around a distal end of the support member.

19. The catheter of claim 14, wherein the distal assembly includes a fluid chamber between the flex circuit and the support member.

* * * * *